United States Patent [19]

Dunberger et al.

[11] Patent Number: 5,399,160

[45] Date of Patent: Mar. 21, 1995

[54] IRRIGATION TUBING SET HAVING COMPLIANT SECTIONS

[75] Inventors: Ulf B. Dunberger, Portsmouth, N.H.; Thomas D. Egan, Marblehead, Mass.; Harpreet Kaur, Woodbury, Minn.

[73] Assignee: Minnesota Mining and Manufacturing Company, St. Paul, Minn.

[21] Appl. No.: 233,309

[22] Filed: Apr. 26, 1994

Related U.S. Application Data

[63] Continuation of Ser. No. 771,616, Oct. 4, 1991, abandoned.

[51] Int. Cl.$^6$ ............................................. A61M 1/00
[52] U.S. Cl. ..................................... 604/31; 604/28; 604/118; 604/247
[58] Field of Search ................ 604/27, 28, 30, 31, 604/5, 34, 118, 123, 151, 153, 246, 247, 250, 280

[56] References Cited

U.S. PATENT DOCUMENTS

| | | | |
|---|---|---|---|
| 3,900,022 | 8/1975 | Widran | 128/7 |
| 3,930,505 | 1/1976 | Wallach | 128/305 |
| 3,986,956 | 10/1976 | Anno | 604/5 |
| 4,077,882 | 3/1978 | Gangemi | 210/90 |
| 4,117,843 | 10/1978 | Banko | 128/230 |
| 4,180,074 | 12/1979 | Murry et al. | 128/276 |
| 4,226,124 | 10/1980 | Kersten | 73/706 |
| 4,261,360 | 4/1981 | Perez | 128/230 |
| 4,314,480 | 2/1982 | Becker | 73/706 |
| 4,335,717 | 6/1982 | Bujan et al. | 604/34 |
| 4,490,135 | 12/1984 | Troutner | 604/5 |
| 4,604,089 | 8/1986 | Santangelo et al. | 604/30 |
| 4,650,462 | 3/1987 | DeSatnick et al. | 604/30 |
| 4,681,559 | 7/1987 | Hooven | 604/9 |
| 4,781,687 | 11/1988 | Wall | 604/118 |
| 4,820,265 | 4/1989 | DeSatnick et al. | 604/30 |
| 4,902,277 | 2/1990 | Mathies et al. | 604/67 |
| 4,940,457 | 7/1990 | Olson | 604/30 |
| 4,973,311 | 11/1990 | Iwakoshi et al. | 604/119 |
| 4,998,914 | 3/1991 | Wiest et al. | 604/67 |
| 5,000,733 | 3/1991 | Mathies et al. | 604/67 |
| 5,006,109 | 4/1991 | Douglas et al. | 604/26 |
| 5,019,038 | 5/1991 | Linden | 604/49 |
| 5,032,112 | 7/1991 | Fairchild et al. | 604/123 |
| 5,037,386 | 8/1991 | Marcus et al. | 604/43 |
| 5,047,010 | 9/1991 | Ams et al. | 604/26 |
| 5,053,002 | 10/1991 | Barlow | 604/30 |

FOREIGN PATENT DOCUMENTS 8600534  1/1986  WIPO .

OTHER PUBLICATIONS

J. Gillquist "Actue Knee Arthroscopy"; O'Conner's Textbook of Arthroscopic Surgery pp. 169-178.

Primary Examiner—John D. Yasko
Attorney, Agent, or Firm—Gary L. Griswold; Walter N. Kirn; Stephen W. Bauer

[57] ABSTRACT

An irrigation system including a pump that regulates the supply of fluid to an endoscopic surgical site, and a tubing set for supplying the fluid. The tubing set comprises an inflow line for supplying fluid to the surgical site, and an outflow line for draining fluid from the surgical site. At least one of the inflow and outflow lines includes an expandable compliant tubing segment that expands to accommodate changes in the rate of fluid flow through the surgical site to reduce variations in fluid pressure in the surgical site. The fluid volume within the compliant tubing segment increases in response to increasing fluid pressure within the compliant tubing segment. The system is particularly designed for use in small joint arthroscopy (e.g., of the wrist) where the fluid volume in the surgical site is relatively small.

32 Claims, 4 Drawing Sheets

IRRIGATION TUBING SET HAVING COMPLIANT SECTIONS

This application is a continuation of U.S. patent application Ser. No. 07/771,616, filed Oct. 4, 1991, now abandoned.

BACKGROUND OF THE INVENTION

The invention broadly relates to endoscopic surgical procedures, and more particularly to an irrigation system and tubing set for use in irrigating an endoscopic surgical site.

A trend in modern medicine has been to treat the body without invasive procedures if at all possible, because invasive procedures inflict a certain trauma of their own on the patient, and because when the skin is broken the risk of infection of the patient, or others by the patient, increases substantially. When surgery must be performed, it is currently considered desirable to use "minimally invasive" procedures as much as possible. A specific known example of a class of such techniques is arthroscopic surgery, wherein joints (most commonly the knee) and their supporting structures are treated through small incisions using tools to visualize the interior of the body.

During such surgery, irrigation of the joint is necessary for the following reasons:

(1) Inflation of the joint is desirable for better visualization and access achieved by an increased joint or tissue separation. This is accomplished by application of pressure through the medium of the irrigation fluid or gas.

(2) Flow of the irrigation fluid through the joint keeps the field of view clear and eliminates loose debris.

(3) The fluid keeps the joint lubricated and replaces lost body fluids.

Co-assigned U.S. Pat. No. 4,650,462 (DeSatnick et al.) discloses an irrigation system particularly adapted for the control of such irrigation, and which allows independent control of both the pressure and the flow. The DeSatnick '462 patent shows an expansion chamber connected to an outflow line for dampening pressure variations. Co-assigned U.S. Pat. No. 4,820,265 (DeSatnick et al.) discloses a tubing set particularly adapted to deliver irrigation fluids as part of such a system. An irrigation system generally as disclosed in the Desatnick et al. patents has been available as Model 8300 under the trade designation "3M ARTHROSCOPY PUMP" from Minnesota Mining and Manufacturing Company, St. Paul, Minn.

U.S. Pat. Nos. 4,604,089 (Santangelo et al.), and 4,940,457 (Olson), and PCT Publication No. WO 86/00534 show other irrigation systems for use during arthroscopy.

While irrigation systems of the type described above have enjoyed success in helping to carry out surgery on large joints such as the knee, it would be desirable to have an irrigation system that is particularly designed to control the irrigation of small joints such as the wrist. The small volume in such joints makes controlling the pressure a more difficult task, since relatively small amounts of flow can translate into large pressure spikes within the joint space.

SUMMARY OF THE INVENTION

The invention provides an irrigation system and tubing set that are particularly useful in irrigating an endoscopic surgical site having a relatively small internal volume, such as an arthroscopic surgical site in a small joint (e.g., a wrist). The irrigation system and tubing set are particularly adapted to reduce the amplitude of pressure peaks and control the fluid pressure of the irrigating fluid. The invention also includes a cannula that is designed for use in the irrigation system, and which is designed for use in small joint arthroscopy. The invention normally includes the use of a pump for regulating the flow of irrigating fluid through the tubing set.

Generally, the tubing set of the invention comprises an inflow line for supplying fluid to the surgical site, and an outflow line for draining fluid from the surgical site. The inflow line is adapted for mounting an inflow cannula in fluid communication with the inflow line to supply fluid to the surgical site, and for connection to a source of fluid in fluid communication with the inflow line so that fluid from the source of fluid can be directed through the inflow cannula. The outflow line is adapted for mounting an outflow cannula in fluid communication with the outflow line to drain fluid from the surgical site. The inflow and outflow lines define a fluid pathway through the surgical site. Inline compliance means is provided in at least one of the inflow and outflow lines for accommodating changes in the rate of fluid flow through the surgical site to reduce variations in fluid pressure in the surgical site. The inline compliance means includes means for increasing the fluid volume within the inline compliance means in response to increasing fluid pressure within the compliance means thereby reducing variations in fluid pressure.

Preferably, the inline compliance means is provided at least in the inflow line, although it is most preferred to provide the compliance means in both the inflow and outflow lines. The compliance means preferably comprises a resilient tubing segment defining a portion of the inflow line. The tubing segment has a cross section that is resiliently expandable in response to increasing fluid pressure within a range to increase the volume of fluid within the tubing segment.

The tubing set preferably includes a means associated with the tubing set for transmitting information about fluid pressure within the surgical site. For example, the means for transmitting information about fluid pressure within the surgical site may comprise a fluid pressure sensing line adapted to be connected in fluid communication with one of the inflow cannula, outflow cannula or a separate pressure sensing cannula. In this case, the pressure sensing line would include: (a) an elongate tubular pressure chamber in the pressure sensing line having a distal end adapted to be connected to one of the inflow cannula, outflow cannula or a separate pressure sensing cannula, and a proximal end mounted in pressure transmitting communication with the remainder of the pressure sensing line; and (b) a pressure transmitting resiliently flexible diaphragm within the pressure chamber, the diaphragm defining a fluid seal within the pressure chamber precluding passage of fluid from the surgical site through the proximal end of the pressure chamber. The remainder of the pressure sensing line defines a column of pressure transmitting fluid (e.g., air) responsive to but segregated from the fluid from the surgical site, and the end of the pressure sensing line opposite the pressure chamber is adapted to be connected in fluid communication with a mechanism for sensing pressure.

The method of irrigating an endoscopic surgical site in a patient with fluid generally comprises providing an irrigation system comprising (1) a tubing set comprising (a) an inflow line for supplying fluid to the surgical site, the inflow line being adapted for connection to a source of fluid; (b) an outflow line for draining fluid from the surgical site; and (c) compliance means provided in at least one of the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means; and (2) a pump adapted to receive a portion of the inflow line to pump fluid through the inflow line. Inflow and outflow cannulae are connected to the inflow and outflow line respectively, and the inflow and outflow cannulae are inserted into the patient to establish a fluid pathway through the surgical site with the tubing set. The irrigation fluid is introduced into the surgical site via the inflow line and cannula, and the irrigation fluid drained out from the surgical site through the outflow cannula and line. The fluid volume is allowed to increase within the compliance means in response to increasing fluid pressure within the compliance means, and to decrease within the compliance means in response to decreasing fluid pressure within the compliance means.

Other features will be in part apparent and in part pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
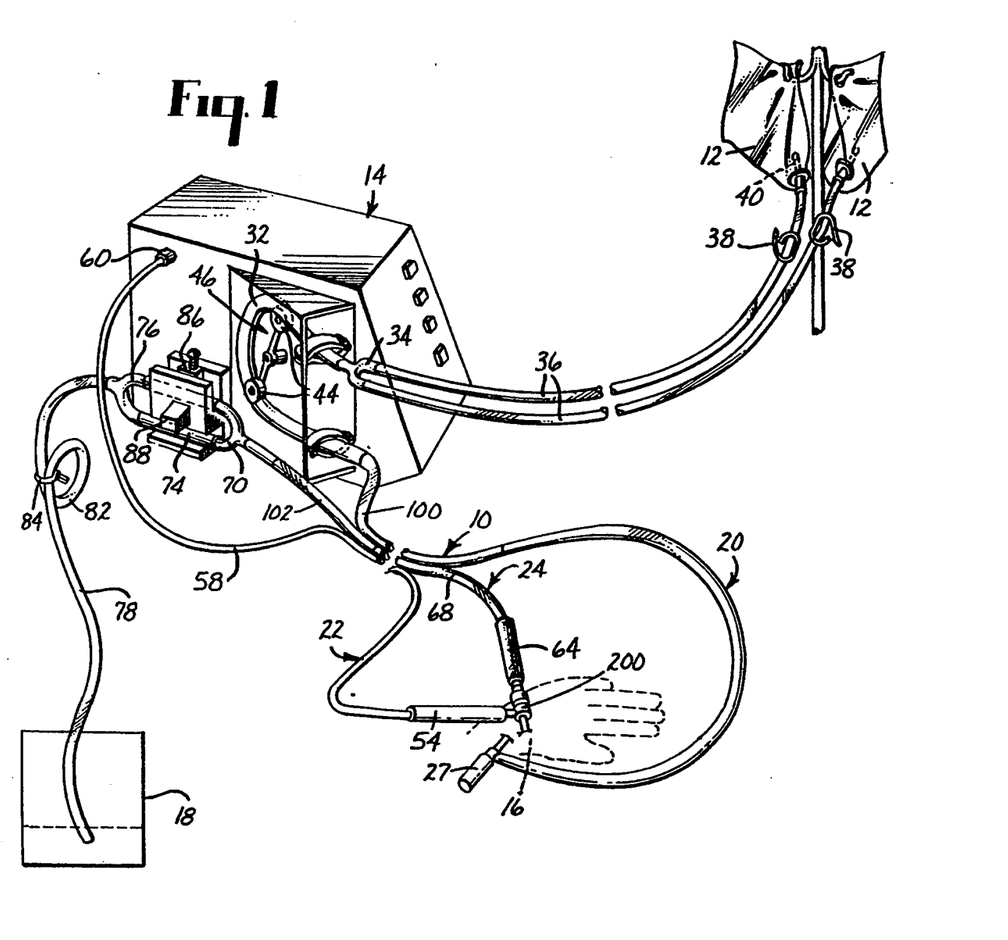
FIG. 1 is a perspective view of an irrigation system of the invention.

As illustrated in FIG. 1, the arthroscopy tubing set 10 of the invention functions as a component of an irrigation system in arthroscopic procedures. The tubing set 10 channels a flow of saline solution from hanging bags or bottles 12 through an arthroscopy pump 14 to the joint or site 16 of the procedure, at a flow rate and pressure set on the pump 14. The pump 14 may be of the "positive displacement" type which normally pump a fixed volume of fluid through each pumping cycle or revolution of a peristaltic pumping roller mechanism 44. Ultimately, the flow discharges to an appropriate collector 18.

Figure 2:
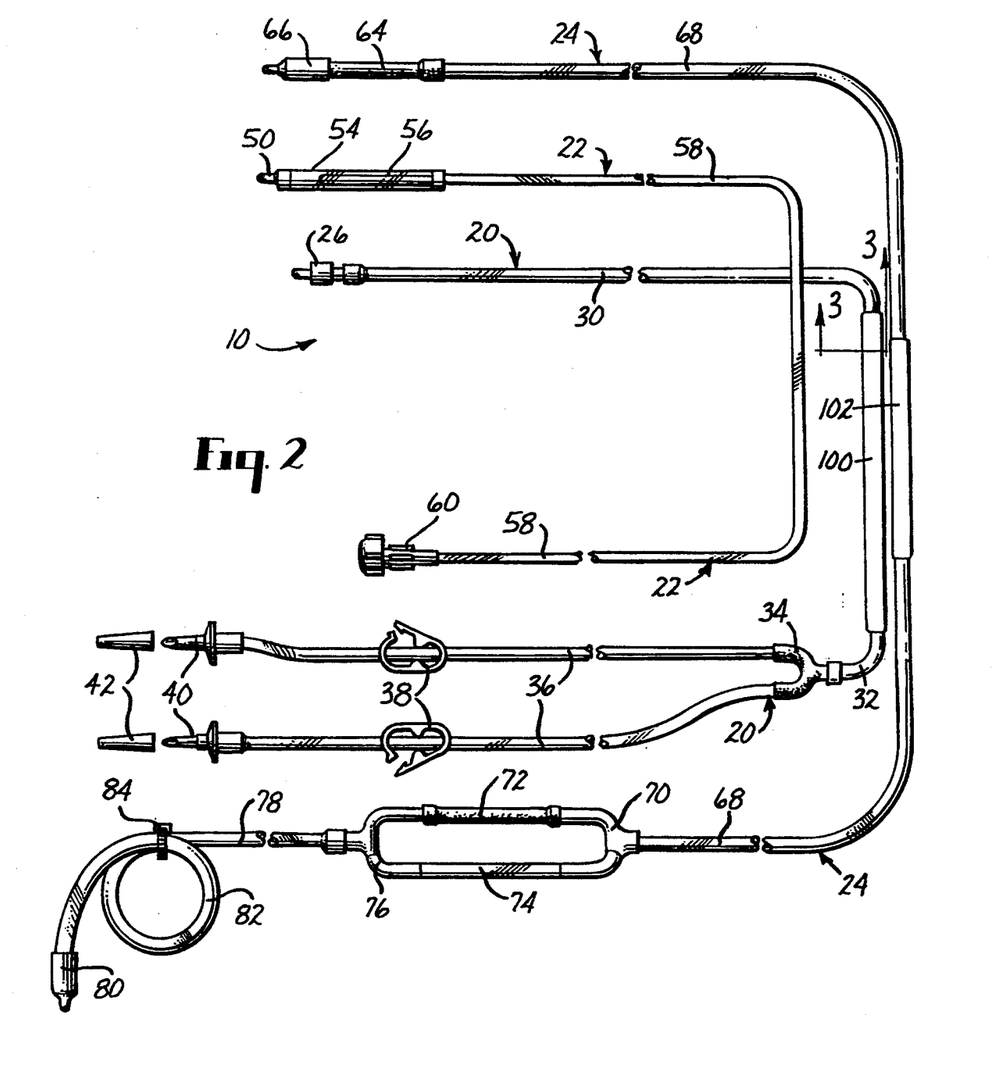
FIG. 2 is a schematic view of a tubing set used in the irrigation system of FIG. 1.

In order to facilitate handling of the tubing set 10, it is preferred that the tubing set 10 be of a trilumen configuration with three parabounded PVC tubes separated at their ends to form three functionally different lines, an inflow line 20, a pressure sensing line 22 and an outflow line 24. Co-assigned U.S. Pat. Nos. 4,650,462 and 4,820,265 (DeSatnick et al.), which disclose an irrigation system and tubing set of the general type described herein, are incorporated herein by reference.

As described in U.S. Pat. No. 4,820,265, the inflow line 20 includes a capped male luer fitting 26 at the patient end. The luer fitting 26 is adapted for connection to an inflow cannula 27. The inflow cannula 27 may be of the general type (although possibly scaled down for small joint surgery) as disclosed in co-assigned U.S. Pat. No. 5,037,386, which is incorporated herein by reference. The fitting 26 is bonded into a delivery tube 30, which is in turn attached to one end of a novel high compliance tubing segment 100 that is described in more detail below. The other end of the high compliance tubing segment 100 is attached to a polyvinyl chloride (PVC) header tube 32.

The header tube 32 connects to a "Y" connector 34 normally formed or cast from plastisol. Two duplicate PVC supply tubes 36 extend from the "Y" connector. A hand manipulable shut-off clamp 38 mounts on each supply tube 36, and the terminal end of each of the supply tubes 36 is bonded to a separate bag spike 40. Each of the bag spikes 40 is provided with a cap or protector 42 which is removed prior to a piercing engagement of the spike 40 into one of the saline containers 12.

The header tube 32 is engageable about the rollers 44 of the peristaltic unit 46 of the pump 14 to pump fluid through the inflow line 20. The rigidity or stiffness and diameter of the header tube 32 are important to the proper operation of the rollers 44 of the peristaltic pump 14. Preferably, the header tube 32 has a durometer of approximately 68 on the Shore A scale, an inside diameter of approximately 0.375 inches (9.5 mm) and an outside diameter of approximately 0.5 inches (12.7 mm).

The pressure sensing line 22 includes a capped male luer pressure retaining fitting 50 bonded into one end of an elongate tubular PVC pressure chamber 54. The pressure chamber 54 contains a resiliently collapsible elongate balloon diaphragm 56 of an appropriate elastomer such as natural or synthetic latex or silicone rubber. The diaphragm 56 is a pressure transmitter and fluid barrier, and is bonded to and in fluid communication with a length of pressure-transmitting tube 58 projecting from the end of the pressure chamber 54 remote from the luer fitting 50. The end of the pressure-transmitting tube 58 remote from the pressure chamber 54 is provided with a cap 60, and is adapted for connection to a mechanism for sensing pressure, such as a pressure transducer (not shown) in the pump 14. This pressure-transmitting tube 58 functions as a pressure tube 58 to transmit sensed pressure, that is, it defines a column of pressure transmitting fluid (e.g., air) responsive to but segregated from the fluid from the surgical site.

Figure 4:
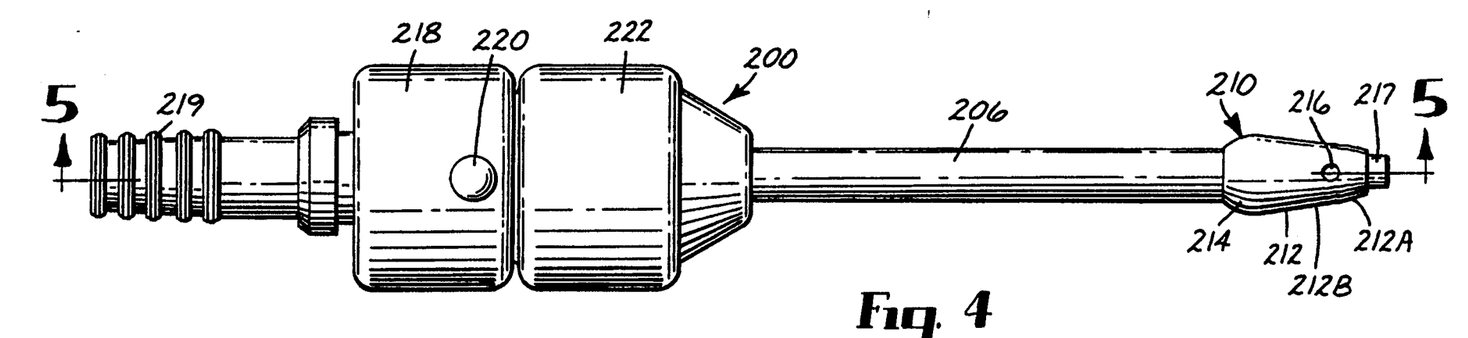
FIG. 4 is a top plan view of a pressure sensing outflow cannula preferably used with the irrigation system of FIG. 1.
Figure 5:
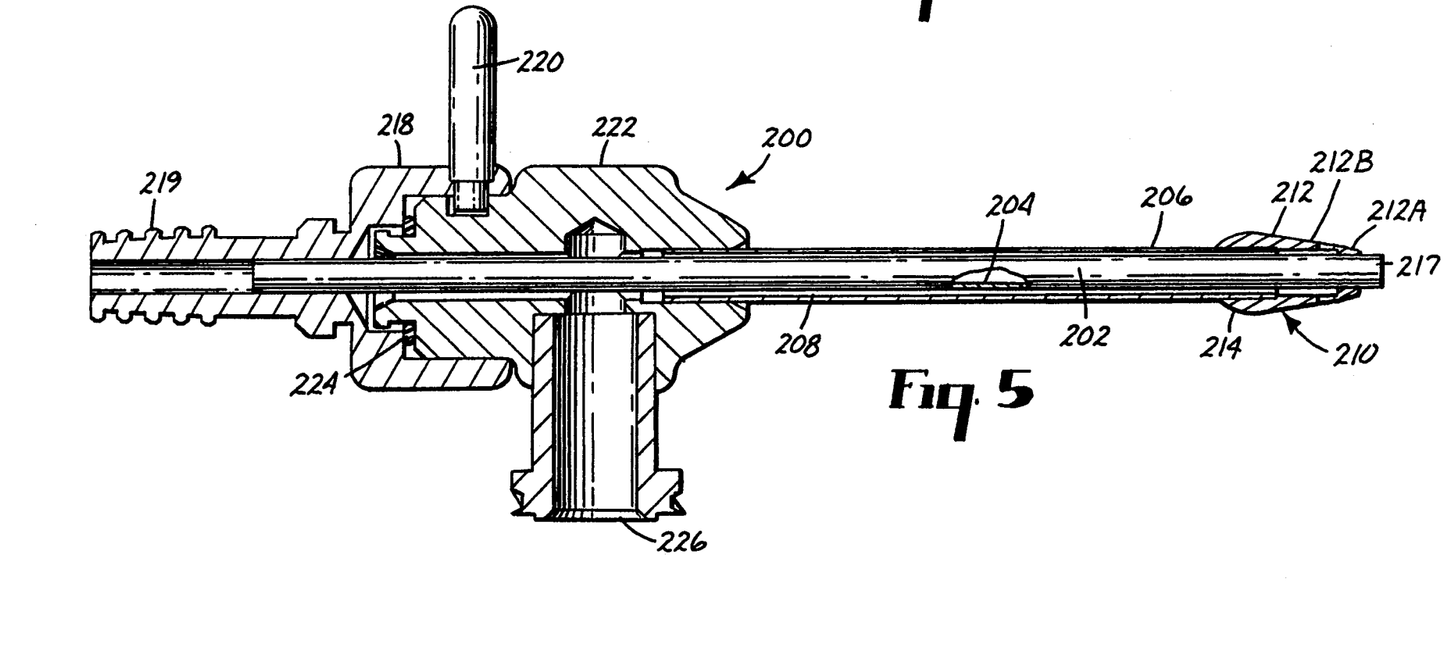
FIG. 5 is a cross-sectional view taken substantially along line 5—5 in FIG. 4.

The luer fitting 50 of the pressure tube 58 would be provided with a capped female luer fitting bonded thereto (not shown), and is adapted to be connected in fluid communication with one of a separate pressure sensing cannula, a pressure sensing inflow cannula, or the pressure sensing outflow cannula 200 shown in FIGS. 1 and 4–5. The pressure sensing line 22 is basically dry, restricting liquid to the diaphragm-containing chamber 54 immediately adjacent the operating site. Fluid pressure sensing line 22 constitutes one embodiment of a means associated with the tubing set 10 for transmitting information about fluid pressure within the surgical site.

The outflow line 24 includes a tubular elastomeric adapter 64 of natural or synthetic latex or silicone rubber at the patient end, which is adapted for connection to an outflow cannula, such as the pressure sensing outflow cannula designated by the reference numeral 200. The outer or free end of the adapter 64 is provided with a protective cap 66 of a distinctive color, preferably blue, providing an easily distinguished visual indication of the patient end of the tubing set 10. The elastomer adapter 64 is bonded to a drain tube 68, which is in turn is bonded a plastisol "Y" connector 70, the two branches of which are bonded to a pair of parallel tubes. The first tube 72 is an elastomer tube, for example of latex or silicone rubber, and the second tube 74 is PVC tubing with a durometer of 39 on the Shore A scale. The two parallel tubes 72 and 74 are rejoined by a second plastisol "Y" connector 76 which in turn is bonded to and in communication with a discharge tube 78. The free remote end of the discharge tube 78 is provided with a distinctively colored cap 80, preferably red and easily distinguished from the opposed end cap 66, again to provide a ready and immediate identification of each end of the tubing set 10.

Approximately 30 inches (760 mm) from the capped end of the tube 78, the discharge tube 78 is provided with one complete coil 82. The coil 82 defines a "pigtail" configuration forming a liquid seal. An appropriate cable tie or the like 84 is wrapped around the coil to retain the configuration thereof. Preferably, the diameter of the discharge tube 78 immediately downstream (toward the remote end at 80) of the coil 82 is larger than the diameter of the discharge tube 78 along the coil 82 and upstream of the coil. For example, the inside diameter of the discharge tube 78 along the coil 82 and upstream from the coil may be approximately ⅛" (3.2 mm), and the inside diameter of the discharge tube 78 downstream of the coil 82 may be approximately ⅜" (9.5 mm).

The preferred arrangement is that the parallel branches or tubes 72 and 74 are positioned upstream relative to the coil 89. As described in U.S. Pat. No. 4,820,265, the parallel tubes 72 and 74 in the outflow line 24 constitute a portion of a pressure control and relief assembly, and are respectively engaged by a mechanical pressure relief valve 86 and a solenoid control valve 88.

The inflow line 20, outflow line 24 and pressure sensing line 22 are preferably joined along a substantial portion thereof in substantially parallel, non-communicating relationship. For example, the three lines 20, 22 and 24 may include portions that have been co-extruded to form one trilumen tube (not shown), or in the case of PVC tubing, the joined portions may be solvent bond with cyclohexanone, for example. It is believed that by joining substantial portions of the tubing set 10 together, confusion during use and set-up is reduced.

A novel inline compliance means (e.g., flattened tubing segments 100 and 102) is provided in at least one of the inflow and outflow lines 20 and 24 for accommodating changes in the rate of fluid flow through the surgical site to reduce variations in fluid pressure in the surgical site. The inline compliance means includes a means for increasing the fluid volume within the compliance means in response to increasing fluid pressure within the compliance means. Preferably, the inline compliance means is provided in both the inflow and outflow lines 20 and 24, although it is also contemplated that the compliance means might be provided in only one of the inflow or outflow lines 20 or 24, in which case it would be preferred to have the compliance means provided in the inflow line 20.

The compliance means conveniently comprises a "first" resilient tubing segment 100 defining a portion of the inflow line 20. The ends of the resilient tubing segment 100 may be bonded to separate portions of the delivery tube 30 to form a part of the delivery tube 30, or one end of the tubing segment 100 may be bonded to the end of the delivery tube 30 and the other end of the tubing segment 100 may be bonded to the downstream end of the header tube 32 as illustrated in FIGS. 1 and 2. The compliant tubing segment 100 should be downstream from the header tube 32 so that in use the tubing segment 100 is along the fluid pathway between the pump 14 and the endoscopic surgical site.

Figure 3A:
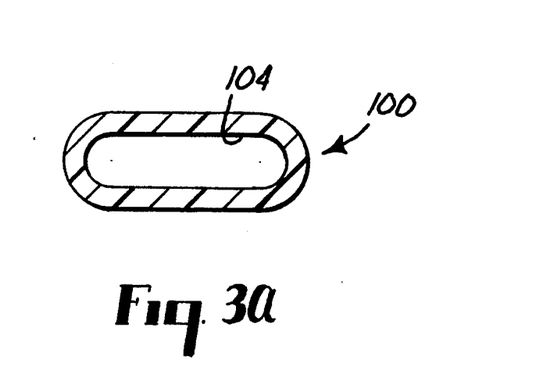
FIG. 3a is a cross-sectional view taken along line 3—3 in FIG. 2, illustrating the normal flattened cross section of a resilient tubing segment forming the compliance means of the tubing set and irrigation system.
Figure 3B:
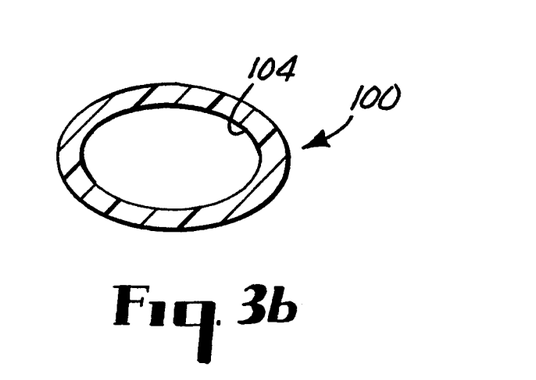
FIG. 3b is a cross-sectional view similar to FIG. 3a illustrating expansion of the flattened cross section of the compliance means in response to increased fluid pressure.
Figure 3C:
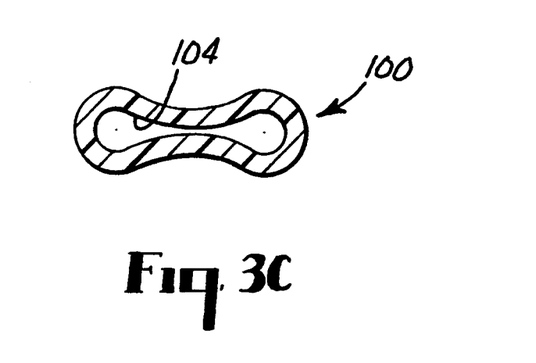
FIG. 3c is a cross-sectional view similar to FIGS. 3a and 3b, illustrating another cross-sectional configuration of the unexpanded compliant tubing segment.

The first compliant tubing segment 100 has a cross section that is resiliently expandable in response to increasing fluid pressure within a range to increase the volume of fluid within the tubing segment 100. This feature helps to minimize variations in fluid pressure. For example, the cross-section of the compliant tubing segment 100 may be generally flattened, rectangular, oval-shaped or dumbbell-shaped when not expanded by relatively high fluid pressure as indicated in FIG. 3a and 3c. The cross sectional configurations shown in FIGS. 3a and 3c are believed to be particularly desirable because the cross sectional area can be increased by flexing the tube wall outwardly without substantial stretching of the tube wall. In other words, the cross section shown in FIGS. 3a and 3c are believed to provide a more responsive tubing segment 100 as far as increasing fluid volume in response to increasing pressure is concerned.

The "second" resilient compliant tubing segment 102 defines a portion 102 of the outflow line 24, and is of a design similar to the first compliant tubing segment 100. As is the case with the first tubing segment 100, the second tubing segment 102 has a cross section that is resiliently expandable in response to increasing fluid pressure within a range to increase the volume of fluid within the second tubing segment 102. The cross sectional configuration of the second tubing segment 102 when unexpanded is preferably as illustrated in FIGS. 3a and 3c, and of similar dimensions and materials as the first tubing segment 100.

As shown in FIG. 2, the second tubing segment 102 can be bonded to the drain tube 68 to form a section 102 of the drain tube 68. Preferably, however, the downstream end of the drain tube 68 is bonded to the upstream end of the high compliance tubing segment 102, and the downstream end of the tubing segment 102 is directly bonded to the "Y" connector 70. The preferred arrangement reduces the number of bonds required by one. The compliant tubing segment 102 should, however, be positioned between the patient and the Y connector 70 for optimal operation of the irrigation system. This arrangement is important for the second tubing segment's optimum response to pressure variations between the patient and the mechanical relief valve 86 and solenoid control valve 88.

Most preferably, the first tubing segment 100 has a length along the inflow line 20 approximately fifty percent longer than the length of the second tubing segment 102 along the outflow line 24 so that, assuming equal cross sectional areas, the amount of the increase in volume within the first tubing segment 100 is approximately fifty percent greater than the amount of the increase in volume within the second tubing segment 102 in response to the same increase in pressure within the first and second tubing segments 100 and 102. For example, the first tubing segment 100 may have a length of approximately 90 cm, and the second tubing segment 102 may have a length of approximately 60 cm.

The resilient tubing segments 100 and 102 are formed of elastomeric material (e.g., polyvinyl chloride (PVC)) having a durometer of less than 60 on the Shore A scale, preferably within the range of approximately 50–60 on the Shore A scale. For example, the resilient tubing segments 100 and 102 may have a durometer on the Shore A scale of approximately 55. In this example, the lumen 104 of the tubing segment 100 (102) may have a generally oval or rectangular cross section as shown in FIG. 3a when unexpanded, with a dimensions of the lumen being approximately 12 mm by 3 mm and the wall thickness of the tubing segments 100 and 102 being about 0.75 mm. In this example, the length of the first tubing segment 100 is 90 cm and the length of the second tubing segment 102 is 60 cm.

The outflow cannula 200 is adapted to be inserted in a patient into the surgical site, and connected in fluid communication with the outflow line 24. The outflow cannula 200 shown in FIGS. 4 and 5 is a double sheathed pressure sensing cannula 200 having (a) an inner sheath 202 defining an inner lumen 204, which is intended to be in fluid communication with the outflow line 24, and (b) an outer sheath 206 defining an outer lumen 208 that receives the inner sheath 202. The portion of the outer lumen 208 not occupied by the inner sheath 202 defines a pressure transmitting passageway (at 208) adapted for fluid communication with the pressure sensing line 22. The inner and outer sheaths 202 and 206 are formed of stainless steel.

The inner and outer sheaths 202 and 206 comprise generally cylindrical hollow shafts. The outer sheath 206 has an enlarged distal end portion 210 that is inserted into the patient to drain the irrigating fluid from the surgical site. The distal end portion 210 of the outer sheath 206 has a tapered portion 212 that is tapered in the distal direction (right in FIGS. 4 and 5) to facilitate insertion into the patient. The distal end portion 210 also has a rounded portion 214 proximally of the tapered portion 212. The rounded portion 214 is generally rounded in the proximal direction radially inwardly toward the remainder of the shaft 206 to help retain the distal end portion 210 within the patient while permitting intentional removal of the outflow cannula 200 from the patient. The distal end portion 210 of the cannula 200 may be considered to be generally acorn shaped.

The distal end portion 210 of the outer sheath 206 includes walls in the tapered portion 212 that form a plurality (e.g., 4) of openings 216 in fluid communication with the pressure transmitting passageway 208.

The openings 216 are preferably arranged in an equally spaced circumferential array in a second or proximal section 212B of the tapered portion 212. As illustrated in FIG. 5, the distal end of the tapered portion 212 converges toward the inner sheath 202 to substantially close the distal end of the outer lumen 208 to fluid communication except through the openings 216. This feature, in combination with preferred design in which the distal end 217 of the inner sheath 202 extends distally (rightwardly in FIGS. 4 and 5) slightly beyond the distal end of the outer sheath 206, helps to isolate the pressure transmitting passageway 208 from the flow of fluid through the inner lumen 204 of the outflow cannula 200.

The tapered portion 212 preferably has two tapered sections 212A and 212B, including a first tapered section 212A extending substantially to the distal end of the outer sheath 206, and a second tapered section 212B extending between the rounded portion 214 and the first tapered section 212A. The angle of taper of the first tapered section 212A is most preferably substantially steeper than the angle of taper of the second tapered section 212B. For example, the included angle defined by the first tapered section 212A may be approximately 43 degrees and the included angle of the second tapered section 212B may be approximately 15 degrees.

The cannula 200 would be provided with a suitable introducer or obturator (not shown) for facilitating insertion of the cannula 200 into the patient. The obturator is inserted into the inner lumen 204 of the cannula 200, and should extend slightly beyond the distal end 217 of the inner sheath 202. The obturator and proximal end of the inner sheath 202 are preferably adapted for a threaded connection between them.

The inner sheath 202 conveniently has a hub 218 generally adjacent its proximal end 219. The hub 218 includes a suitable releasable locking mechanism, such as a the bayonet mechanism illustrated in FIG. 5, for locking the inner sheath 202 in position in the outer sheath 206. For example, the pin portion of the bayonet mechanism is provided by an inward extension of a lever or handle 220 provided on the hub 218 for manually turning the inner sheath 202 relative to the outer sheath 206 to lock them together. An L-shaped, pin-receiving channel is provided in the hub 222 of the outer sheath 206 to complete the bayonet mechanism. An O-ring seal 224 is provided in the hub 222 of the outer sheath 206 to form a seal between the hubs 218 and 222.

As illustrated in FIG. 2, the proximal end 219 of the inner sheath 202 is adapted for connection to the upstream end of the outflow line 24. The side port 226 is adapted for connection of the pressure sensing line 22 in order to bring the fluid side of the pressure chamber 54 into fluid communication with the pressure-transmitting passageway 208.

OPERATION

In installing the tubing set 10 prior to commencing the arthroscopic procedure, the pump 14 is initially put in the off position and saline bags 12 hung just above the level of the pump 14. Using sterile techniques, the tubing set 10 is delivered to the scrub nurse. The scrub nurse, in turn, will pass the red-capped equipment end of the tubing set 10 to the circulating nurse. The scrub nurse will then secure the excess tubing and the blue-capped patient end of the tubing to the sterile field on the draped patient. The circulating nurse will close the clamps 38 on the inflow line 20. The inflow line 20 will then be connected to the pump 14 by engaging the header tube 32 around the pump rollers 44. To facilitate this installation, flow direction indicating arrows can be provided on the pump 14. The bag spikes 40 will be connected to the saline bags 12.

The pressure sensing or monitoring line 22 will be connected to the appropriate port on the pump 14 and subsequently connected to the patient cannula 200. If the pressure sensing outflow cannula 200 is being used, the pressure sensing line 22 is connected to the side port 226, and the blue-capped patient end of the outflow line 24 is connected to the proximal end 219. The downstream end of the inflow line 20 is connected to the appropriate port of an inflow cannula 27, which may be of the type that is adapted to receive an optical scope (not shown) suitable for use with a video display terminal (not shown).

With regard to the outflow line 24, and in particular the pressure control and relief assembly comprising the parallel lines 72 and 74, the relatively stiffer PVC control tube 74 is mounted in operative position within the solenoid valve assembly as. The relatively more flexible elastomer pressure relief tube 72 is in turn inserted in operative position within the mechanical relief valve unit 86. Directional arrows may be provided in conjunction with the valve units to insure proper directional positioning of the tubes 72 and 74.

Finally, the discharge tube 78 is placed within an appropriate collector or liquid collecting receptacle 18 open to the ambient air. The irrigation system, with a new sterile tubing set 10 installed, is now ready for use.

In use, the inflow and outflow cannulae 27 and 200 are inserted into the patient to establish a fluid pathway through the surgical site. Irrigation fluid (e.g., saline solution) is then introduced into the surgical site via the inflow line 20 and inflow cannula 27, and drained from the surgical site through the outflow cannula 200 and outflow line 24. Pressure within the surgical site is indicated at the pump 14 as transmitted through the pressure sensing line 22.

During operation of the irrigation system, the fluid volume is allowed to increase within the compliant tubing segments 100 and 102 in response to increasing fluid pressure, and the fluid volume within the compliant tubing segments 100 and 102 is allowed to decrease in response to decreasing fluid pressure. This is accomplished by allowing the cross section of the resilient tubing segments 100 and 102 to expand in response to the increasing fluid pressure within a range of expansion. The flattened portions of the tubing segment 100, 102 expand away from each other to increase the fluid volume within the tubing segment 100, 102 in response to increasing pressure.

Example 1

A tubing set 10 generally as shown in the figures was prepared, with the compliant tubing segments 100 and 102 formed of polyvinyl chloride compounded to a durometer of 55 on the Shore A scale. The tubing was fabricated by extrusion. The interior lumen of the compliant tubing segments 100 and 102 was formed in the shape of an oval, and the dimensions of the cross section of the lumen were 12 mm by 3 mm. The wall thickness of each of the compliant tubing segments 100 and 102 was the same (0.75 mm). The length of the compliant tubing segment 100 in the inflow line 20 was 90 cm, and the length of the compliant tubing segment 102 in the outflow line 24 was 60 cm.

The tubing set 10 was connected to a Model 8300 "3M ARTHROSCOPY PUMP" commercially available from Minnesota Mining and Manufacturing Company, St. Paul, Minn. The bag spikes 40 were used to pierce and engage bags 12 of normal saline solution. Arthroscopic surgery was performed on the wrist joint of a fresh cadaver. Fluid pressure within the joint was observed to be within the norms expected of standard tubing sets operating on larger joint spaces. Excessive pressure spikes were not observed.

As various changes could be made in the above constructions and methods without departing from the scope of the invention, it is intended that all matter contained in the above description or shown in the accompanying drawing be interpreted as illustrative and not in a limiting sense.

We claim:

1. For use in an irrigation system of the type that regulates the supply of fluid to an endoscopic surgical site, a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in both the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means;

the inline compliance means comprising a resilient tubing segment defining a substantial portion of the aforesaid at least one of the inflow and outflow lines, the tubing segment having a generally flattened cross section when not expanded that is resiliently expandable in response to increasing fluid pressure within a range to increase the volume of fluid within the tubing segment and thereby to reduce variations in fluid pressure in the surgical site.

2. For use in an irrigation system of the type that regulates the supply of fluid to an endoscopic surgical site, a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in at least one of the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means;

the inline compliance means comprising a resilient tubing segment defining a substantial portion of the aforesaid at least one of the inflow and outflow lines, the tubing segment having a generally flattened cross section when not expanded that is resiliently expandable in response to increasing fluid pressure within a range to increase the volume of fluid within the tubing segment and thereby to reduce variations in fluid pressure in the surgical site, the resilient tubing segment having a length within the range of approximately 60–90 centimeters.

3. A tubing set according to claim 2 wherein the compliance means is provided in the inflow line.

4. A tubing set according to claim 1 wherein the resilient tubing segment has a generally rectangular cross section when not expanded.

5. For use in an irrigation system of the type that regulates the supply of fluid to an endoscopic surgical site, a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in both of the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means, the compliance means comprising:

a first resilient tubing segment defining a portion of the inflow line, the first tubing segment having a generally flattened cross section when not expanded, the cross section of the tubing segment being resiliently expandable in response to increasing fluid pressure within a range to increase the volume of fluid within the tubing segment; and a second resilient tubing segment defining a portion of the outflow line, the second tubing segment having a cross section that is resiliently expandable in response to increasing fluid pressure within a range to increase the volume of fluid within the second tubing segment.

6. A tubing set according to claim 5 wherein the first tubing segment has a length along the inflow line approximately fifty percent longer than the length of the second tubing segment along the outflow line.

7. A tubing set according to claim 5 wherein the amount of the increase in volume within the first tubing segment is approximately fifty percent greater than the amount of the increase in volume within the second tubing segment in response to the same increase in pressure within the first and second tubing segments.

8. A tubing set according to claim 5 wherein the resilient tubing segment is formed of elastomeric material have a durometer of less than about 60 on the Shore A scale.

9. A tubing set according to claim 8 wherein the material of the resilient tubing segment has a durometer of approximately 50–60 on the Shore A scale.

10. A tubing set according to claim 9 wherein the elastomeric material is a polyvinyl chloride compound.

11. A tubing set according to claim 5 further comprising means associated with the tubing set for transmitting information about fluid pressure within the surgical site.

12. For use in an irrigation system of the type that regulates the supply of fluid to an endoscopic surgical site, a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site;

inline compliance means provided in the inflow line for accommodating changes in the rate of fluid flow through the surgical site to reduce variations in fluid pressure in the surgical site, the compliance means including means for increasing the fluid volume within the compliance means in response to increasing fluid pressure within the compliance means, the compliance means comprising a resilient tubing segment defining a portion of the inflow line, the tubing segment having a generally flattened cross section when not expanded, the cross section of the tubing segment being resiliently expandable in response to increasing fluid pressure within a range to increase the volume of fluid within the tubing segment; and means associated with the tubing set for transmitting information about fluid pressure within the surgical site;

the inflow line, outflow line and means for transmitting information about fluid pressure within the surgical site being joined along a portion thereof in substantially parallel, non-communicating relationship.

13. A tubing set according to claim 12 wherein the means for transmitting information about fluid pressure within the surgical site comprises a fluid pressure sensing line adapted to be connected in fluid communication with one of a pressure sensing inflow cannula, pressure sensing outflow cannula or a separate pressure sensing cannula; the pressure sensing line including:

an elongate tubular pressure chamber in the pressure sensing line having a distal end adapted to be connected to one of the pressure sensing inflow cannula, pressure sensing outflow cannula or a separate pressure sensing cannula, and a proximal end mounted in pressure transmitting communication with the remainder of the pressure sensing line; and a pressure transmitting resiliently flexible diaphragm within the pressure chamber, the diaphragm defining a fluid seal within the pressure chamber precluding passage of fluid from the surgical site through the proximal end of the pressure chamber;

the remainder of the pressure sensing line defining a column of pressure transmitting fluid responsive to but segregated from the fluid from the surgical site; and the end of the pressure sensing line opposite the pressure chamber being adapted to be connected in fluid communication with a mechanism for sensing pressure.

14. An irrigation system for supplying fluid to an endoscopic surgical site, the system comprising:

a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in both the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means, the inline compliance means comprising a resilient tubing segment defining a substantial portion of the aforesaid at least one of the inflow and outflow lines, the tubing segment having a generally flattened cross section when not expanded that is resiliently expandable in response to increasing fluid pressure within a range to increase the volume of fluid within the tubing segment; and a pump adapted to receive a portion of the inflow line to pump fluid through the inflow line.

15. An irrigation system according to claim 14 wherein the pump is a positive displacement pump.

16. An irrigation system for supplying fluid to an endoscopic surgical site, the system comprising:

a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in at least one of the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means, the inline compliance means comprising a resilient tubing segment defining a substantial portion of the aforesaid at least one of the inflow and outflow lines, the tubing segment having a generally flattened cross section when not expanded that is resiliently expandable in response to increasing fluid pressure within a range to increase the volume of fluid within the tubing segment, the resilient tubing segment having a length within the range of approximately 60–90 centimeters; and a pump adapted to receive a portion of the inflow line to pump fluid through the inflow line.

17. An irrigation system according to claim 16 wherein the compliance means is provided in the inflow line.

18. An irrigation system according to claim 16 wherein the resilient tubing segment has a generally rectangular cross section when not expanded.

19. An irrigation system for supplying fluid to an endoscopic surgical site, the system comprising:

a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and inline compliance means provided in both the inflow and outflow lines for accommodating changes in the rate of fluid flow through the surgical site to reduce variations in fluid pressure in the surgical site, the compliance means including means for increasing the fluid volume within the compliance means in response to increasing fluid pressure within the compliance means; and a pump adapted to receive a portion of the inflow line to pump fluid through the inflow line;

the compliance means of the tubing set comprising:

a first resilient tubing segment defining a portion of the inflow line, the first tubing segment having a generally flattened cross section when not expanded that is resiliently expandable in response to increasing fluid pressure within a range to increase the volume of fluid within the tubing segment; and a second resilient tubing segment defining a portion of the outflow line, the second tubing segment having a cross section that is resiliently expandable in response to increasing fluid pressure within a range to increase the volume of fluid within the second tubing segment.

20. An irrigation system according to claim 19 wherein the amount of the increase in volume within the first tubing segment is approximately fifty percent greater than the amount of the increase in volume within the second tubing segment in response to the same increase in pressure within the first and second tubing segments.

21. An irrigation system according to claim 19 wherein the resilient tubing segment is formed of elastomeric material have a durometer of less than about 60 on the Shore A scale.

22. An irrigation system according to claim 21 wherein the material of the resilient tubing segment has a durometer of approximately 50-60 on the Shore A scale.

23. An irrigation system according to claim 19 wherein the tubing set further comprises means associated with the tubing set for transmitting information about fluid pressure within the surgical site.

24. An irrigation system according to claim 23 wherein the means for transmitting information about fluid pressure within the surgical site comprises a fluid pressure sensing line adapted to be connected in fluid communication with one of the inflow cannula, outflow cannula or a separate pressure sensing cannula; the pressure sensing line including:

an elongate tubular pressure chamber in the pressure sensing line having a distal end adapted to be connected to one of the inflow cannula, outflow cannula or a separate pressure sensing cannula, and a proximal end mounted in pressure transmitting communication with the remainder of the pressure sensing line; and a pressure transmitting resiliently flexible diaphragm within the pressure chamber, the diaphragm defining a fluid seal within the pressure chamber precluding passage of fluid from the surgical site through the proximal end of the pressure chamber;

the remainder of the pressure sensing line defining a column of pressure transmitting fluid responsive to but segregated from the fluid from the surgical site; and the end of the pressure sensing line opposite the pressure chamber being adapted to be connected in fluid communication with a mechanism for sensing pressure.

25. A method for irrigating an endoscopic surgical site in a patient with fluid, the method comprising the following steps:

providing an irrigation system comprising (1) a tubing set comprising (a) an inflow line for supplying fluid to the surgical site, the inflow line being adapted for connection to a source of fluid; (b) an outflow line for draining fluid from the surgical site; and (c) inline compliance means provided in at least one of the inflow and outflow lines for accommodating changes in the rate of fluid flow through the surgical site to reduce variations in fluid pressure in the surgical site, the compliance means including means for increasing the fluid volume within the line in response to increasing fluid pressure within the compliance means, the compliance means comprising a resilient tubing segment defining a portion of the inflow line, the tubing segment having a cross section that is resiliently expandable in response to increasing fluid pressure within a range to increase the volume of fluid within the tubing segment;

connecting inflow and outflow cannulae to the inflow and outflow line respectively;

inserting the inflow and outflow cannulae into the patient to establish a fluid pathway through the surgical site with the tubing set;

introducing irrigation fluid into the surgical site via the inflow line and cannula;

draining the irrigation fluid out from the surgical site through the outflow cannula and line;

allowing the fluid volume to increase within the compliance means in response to increasing fluid pressure within the compliance means, and allowing the fluid volume to decrease within the compliance means in response to decreasing fluid pressure within the compliance means, including the step of allowing the cross section of the resilient tubing segment to expand in response to the increasing fluid pressure within a range of expansion.

26. A method according to claim 25 wherein the resilient tubing segment has a generally flattened cross section when not expanded;

the step of allowing the cross section of the resilient tubing segment to expand in response to the increasing fluid pressure within a range of expansion comprising expanding the flattened portions of the tubing segment away from each other in response to increasing fluid pressure to increase the fluid volume within the tubing segment.

27. A method according to claim 26 wherein the irrigation system further comprises a pump adapted to receive a portion of the inflow line to pump fluid through the inflow line; the step of introducing irrigation fluid into the surgical site via the inflow line and cannula including:

pumping irrigation fluid through the inflow line with the pump to deliver the irrigation fluid into the surgical site.

28. For use in an irrigation system of the type that regulates the supply of fluid to an endoscopic surgical site, a tubing set comprising:

an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;

an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and two resilient-compliant tubing segments defining a substantial portion of each of the inflow and outflow lines, the resilient-compliant tubing segment having a generally flattened cross section when not expanded that is expandable to increase the fluid volume within the tubing segment in response to increasing fluid pressure within the tubing segment, thereby accommodating changes in the rate of fluid flow through the surgical site to reduce variations in fluid pressure in the surgical site.

29. A tubing set according to claim 28 wherein the resilient-compliant tubing segment has a generally rectangular cross section when not expanded.

30. For use in an irrigation system of the type that regulates the supply of fluid to an endoscopic surgical site, a tubing set comprising:
an inflow line adapted for supplying fluid to the surgical site, the inflow line being adapted for mounting an inflow cannula in fluid communication with the inflow line to supply fluid to the surgical site, and adapted for connection to a source of fluid in fluid communication with the inflow line so that fluid from the source of fluid can be directed through the inflow cannula;
an outflow line adapted for draining fluid from the surgical site, the outflow line being adapted for mounting an outflow cannula in fluid communication with the outflow line to drain fluid from the surgical site, the inflow and outflow lines defining a fluid pathway through the surgical site; and
a first resilient-compliant tubing segment in fluid communication with the inflow line for accommodating changes in the rate of fluid flow through the surgical site to reduce variations in fluid pressure in the surgical site, the first resilient-compliant tubing segment having a generally flattened cross section when not expanded that is expandable to increase the fluid volume within the tubing segment in response to increasing fluid pressure within the tubing segment; and
a second resilient-compliant tubing segment in fluid communication with the outflow line, the second tubing segment having a cross section that is resiliently expandable in response to increasing fluid pressure within a range to increase the volume of fluid within the second tubing segment.

31. A tubing set according to claim 30 wherein the resilient-compliant tubing segment is formed of elastomeric material have a durometer of less than about 60 on the Shore A scale.

32. A tubing set according to claim 31 wherein the material of the resilient-compliant tubing segment has a durometer of approximately 50–60 on the Shore A scale.

* * * * *

UNITED STATES PATENT AND TRADEMARK OFFICE
CERTIFICATE OF CORRECTION

PATENT NO. : 5,399,160
DATED : March 21, 1995
INVENTOR(S) : Ulf B. Dunberger, Thomas D. Egan and Harpreet Kaur It is certified that error appears in the above-indentified patent and that said Letters Patent is hereby corrected as shown below:

Col. 5, line 52, "89" should read --82--.
Col. 9, line 23, "as" should read --88--.

Signed and Sealed this

Eighth Day of August, 1995

Attest:

BRUCE LEHMAN

Attesting Officer     Commissioner of Patents and Trademarks